United States Patent [19]

Montagnier et al.

[11] Patent Number: 5,677,123
[45] Date of Patent: Oct. 14, 1997

[54] MYCOPLASMAS—AGENTS FOR DETECTING AND CHARACTERIZING MYCOPLASMAS IN VITRO

[75] Inventors: Luc Montagnier, Le Plessis-Robinson; Alain Blanchard, Montrouge; Anne Marie Di Rienzo, Paris; Denise Guetard, Paris; Véronique Rame, Paris, all of France

[73] Assignee: Institut Pasteur, France

[21] Appl. No.: 487,638

[22] Filed: Jun. 7, 1995

Related U.S. Application Data

[63] Continuation of Ser. No. 949,502, filed as PCT/FR91/00397, May 16, 1991, abandoned.

[30] Foreign Application Priority Data

May 18, 1990 [FR] France ................ 90 06285

[51] Int. Cl.$^6$ .................. C12Q 1/70; C12Q 1/68
[52] U.S. Cl. ....................... 435/5; 435/6
[58] Field of Search ............... 435/5, 6, 91.2; 935/77, 78

[56] References Cited

U.S. PATENT DOCUMENTS

| | | | |
|---|---|---|---|
| 4,387,161 | 6/1983 | McGarrity et al. | 435/34 |
| 5,242,820 | 9/1993 | Lo | 435/240 |

FOREIGN PATENT DOCUMENTS

| | | |
|---|---|---|
| 0 250 662 | 6/1986 | European Pat. Off. . |
| 0 250 662 | 1/1988 | European Pat. Off. . |

OTHER PUBLICATIONS

Lo, S-C. et al., "Virus–like infectious agent (VLIA) is a novel pathogenic *mycoplasma incognitus*," Am. J. Tropical Med. and Hygiene, 41(5):586–600 (Nov. 1989).
Amikam, D., et al., "Ribosomal RNA genes in Mycoplasma," Nuc. Acids Res. 10:4215–4222 (1982).
Schneider, E.L., et al., Chem. Abstracts, vol. 80, No. 21, p. 192 (1974).
Laborde, M., "Étude de la sensibilitéaux antibiotiques de 34 souches de mycoplasmes a grandes colonies," Pathologie Biologie, 25(8):541–546 (Oct. 1977).
Amikam, D., et al., "Mycoplasmas (Mollicutes) have a low number of rRNA genes," J. Bacteriology 158(1):376–378 (Apr. 1984).

Barth, O., et al., "Rapid detection by transmission electron microscopy of mycoplasma contamination in sera and cell cultures," Biosis Abstract, Mem. Inst. Oswaldo Cruz 83:63–6 (1988).
Smith, G., et al., "Comparison of two methods for the small–scale extraction of DNA from subgingival microorganisms," Biosis Abstract, Oral icrobiol. Immunol. 4(3):135–140 (1989).
Yogev, D., et al., "Genetic and antigenic distinction of *Mycoplasma pirum* from other mycoplasmas with specialized tip structures," Int. J. of Sys. Bact. 38(2):147–150 (1988).
Saillard, C. et al., "Genetic and serological relatedness between *Mycoplasma fermentans* strains and a mycoplasma recently identified in tissues of AIDS and non–AIDS patients," Res. Virol. 141(3):385–395 (1990).
Res Virol 141(3):385–396 (1990) (biosis Abstract).
Lo et al Am. J. Trop. Med. Hyg 41(5):586–600 (1989) (biosis abstract).
Yogev et al Int. J. of Sys. Bact. 38(2):147–150 (1988).
Amikam et al Nucleic Acid Res. 10:4215–4222.
Barth et al (Biosis Abstract) Mem Inst Oswaldo 83:63–6 (1988).
Smith et al (Biosis Abstract) Oral Microbiol Immunol 4(3):135–140 (1989).
Amikan et al, J. Bacteriology 158:376–378 (1984).
Lo et al., American Journal of Tropical Medicine and Hygiene, vol. 41, No. 5 (Nov. 1989), pp. 586–600.
D. Amikam et al., Nucleic Acids Reserch, vol. 10, No. 14 (1982), pp. 4215–4222.
E.L. Schneider et al., Chemical Abstracts, vol. 80, No. 21 (1974), p. 192.
Laborde et al., Pathologie Biologie, vol. 25, No. 8 (Oct. 1977), pp. 541–546.

*Primary Examiner*—Eggerton A. Campbell
*Attorney, Agent, or Firm*—Finnegan, Henderson, Farabow, Garrett & Dunner, L.L.P.

[57] ABSTRACT

Novel mycoplasmas are described which are prominent in patients who are thought to be suffering from AIDS. Devices are also provided for the in vitro detection of mycoplasmas in a biological fluid by means of a reagent which is specific for the mycoplasma group without being specific for particular species within said group. Devices for testing mycoplasma sensitivity to antibiotics are also described.

9 Claims, 3 Drawing Sheets

MYCOPLASMAS— AGENTS FOR DETECTING AND CHARACTERIZING MYCOPLASMAS IN VITRO

This application is a continuation of application Ser. No. 07/949,502, filed as PCT/FR91/00397 May 16, 1991, now abandoned.

The invention relates to novel mycoplasmas, as well as to agents for detecting and characterizing them.

The mycoplasmas are infectious agents for man often implicated in different diseases. There exist different types of mycoplasmas distinguished according to the diseases in which they occur.

It has already been observed in the case of infection by a HIV retrovirus (HIV: Human Immunodeficiency Virus) responsible for AIDS, that mycoplasmas can be detected in some tissues. Thus Lo et al. detected in the tissues of some patients suffering from AIDS a mycoplasma designated as *M. incognitus* and which exhibits a close relationship with *M. fermentans*, another known mycoplasma (Lo et al. Am. J. Trop. Med. Hyg. 41 (5) 1989 pp. 586–600).

In order to detect this mycoplasma Lo et al. had recourse, on the one hand, to antibodies and, on the other, to a specific nucleotide probe from *M. incognitus*.

Unlike Lo et al., who have put forward the hypothesis concerning the responsibility of a specific mycoplasma in the infection of patients with AIDS and who have developed agents, in particular probes, specific for this mycoplasma in order to detect its presence in tissues of patients the inventors, on the other hand, have observed that the mycoplasmas present in patients infected with the HIV may belong to different types. They have thus investigated the presence of possible mycoplasmas in the blood of patients infected with a HIV retrovirus or suffering from AIDS with agents not specific to a particular mycoplasma.

The inventors have also identified and characterized novel mycoplasmas, present in the blood of patients infected with the HIV thus showing that the infection with HIV may be accompanied by an infection by one or more different mycoplasmas, depending on the patients.

Starting from these observations, the inventors have developed agents designed to detect and isolate mycoplasmas in blood samples taken from patients infected with HIV or in other patients infected with mycoplasmas but not contaminated with the HIV.

In order to define an active treatment against specific mycoplasmas, they have also developed agents to test their sensitivity to medicines, in particular to antibiotics. The invention also enables a follow-up of the patients infected with mycoplasmas to be performed and, where necessary, permits the medical treatment to be adapted to the progress of the infection.

Thus, the object of the invention is novel mycoplasmas related or unrelated to known classes of mycoplasmas present in particular in patients affected by the HIV.

A first mycoplasma according to the invention is the mycoplasma corresponding to the strain ber deposited with the National Collection of Cultures of Microorganisms in Paris (CNCM) under the number I-950 on 3 May 1990 and with the NCIMB on 17 Mar. 1990 under the number 40283.

Another mycoplasma according to the invention is *M. fermentans* No. 8 deposited with the National Collection of Cultures of Microorganisms in Paris (CNCM) under the number I-949 on 3 May 1990 and with the NCIMB on 17 March 1990 under the number 40284.

The mycoplasmas according to the invention are also characterized in that their nucleic acid hybridizes with nucleotide sequences of the genomes of *M. ber* or *M. fermentans* No. 8 under the conditions described by D. Amikam et al., Nucleic Acids Research (1982) vol. 10 No. 14, pp. 4215–4522.

The invention also relates to the use of a nucleotide probe such as that described above for the identification of mycoplasmas in a biological sample taken from a patient likely to be infected with AIDS, in particular by making use of the PCR procedures, or for use in the follow-up treatment of such a patient infected with mycoplasmas.

The invention also relates to probes specific for the group of mycoplasmas but not specific for the species, for the detection of an infection with mycoplasmas.

The mycoplasmas previously described, isolated from patients suffering from the HIV, are responsible for the cytolytic effect induced by the HIV in lymphocytes or in cells of lymphoid lines. Consequently, the isolation and the characterization of mycoplasmas in particular in blood samples taken from patients infected with HIV, may make it possible to have an effect on the pathogenesis of AIDS.

The observation by the inventors of the possibility of detecting mycoplasmas in blood with agents not specific for particular species in the group of the mycoplasmas has given them the opportunity to design agents for detecting, isolating and treating an infection with mycoplasmas in the blood. The agents thus developed by the inventors can be used not only in cases of disease associated with the HIV virus but also in any infection by mycoplasmas, which is expressed by their presence in the blood.

Hence, the object of the invention is a procedure for the in vitro detection of an infection with a HIV or the stages of its progression in an individual suspected to be a carrier of it characterized:

by placing a specific reagent of the group of the mycoplasma but not specific for particular species within this group in contact with a composition itself originating in the biological fluid taken from this patient, this composition being constituted by the biological fluid itself or resulting from the isolation from this sample of a fraction likely to contain mycoplasmas, these latter having been subjected to a prior amplification, if necessary, by the detection of the presence of mycoplasmas in the above-mentioned composition with the aid of the above-mentioned reagent.

According to an advantageous embodiment of the invention, the biological fluid on which the detection is carried out is a blood sample and the composition suspected of containing the mycoplasmas comprises elements represented in the blood, in particular red blood cells or lymphocytes. When the biological fluid is blood, a special detection procedure included in the above definition is characterized in that the following steps are performed prior to the detection of the mycoplasmas:

a) the blood sample is treated in order to separate the red blood cells, which constitute a fraction likely to contain the mycoplasmas and on which the detection is performed, from the other constituents of the blood, b) the red blood cells are separated from the mycoplasmas possibly present by sedimentation of the red blood cells, c) an ultracentrifugation of the supernatant obtained after sedimentation is carried out under conditions likely to cause the sedimentation of the components within the supernatant which are carriers of the mycoplasmas and the pellet obtained after ultracentrifugation is recovered, the above-mentioned detection of the mycoplasmas being performed on the pellet.

For the initial treatment of the red blood cells it is possible to proceed by centrifugation of the blood sample at 400 g for 30 minutes and washing with a defined medium supplemented, if necessary, with antibiotics which are inactive towards the mycoplasmas, this washing medium being, for example, a RPMI 16–40 medium supplemented with 10% fetal calf serum from which complement has been removed beforehand, for example by heating at 56° C. for 30 mn, this serum having been tested for the absence of mycoplasmas.

Advantageously, the centrifugation of the red blood cells is carried out at 1000 g for 5 mn and the ultracentrifugation of the supernatant obtained after centrifugation is performed at 245,000 g for 60 mn.

In the framework for carrying out the above detection starting from red blood cells, the detection of the mycoplasmas possibly present comprises the following step:

the ultracentrifugation pellet obtained in the previous step is inoculated into a culture medium particularly suited to the culture of mycoplasmas, for example a SP-4 medium enriched as described by Tully et al. (Science 1977 195, page 892–894), the detection of the mycoplasmas being then carried out in this medium.

In this case, the detection is carried out directly after placing the composition suspected of containing the mycoplasmas in contact with the culture medium specific for the mycoplasmas, for example a SP-4 medium enriched as above.

Another preferred mode of detection starting from the red blood cells is characterized in that the detection of the presence of mycoplasmas comprises inoculation with the above-mentioned composition and in that the development of an infection of initially healthy lymphocytes by the mycoplasmas of the composition is detected.

In this case, the uncontaminated lymphocytes inoculated by the mycoplasmas are labelled, for example, with radioactive uracil, and the culture supernatant is sedimented to equilibrium in a sucrose density gradient before the incorporation of uracil into the cultures is detected, this incorporation being indicative of the presence of mycoplasmas. Generally speaking, the sedimentation is such that it enables the mycoplasmas to be separated from the other constituents.

This procedure possesses the advantage of being very rapid and very sensitive compared with growth in a synthetic medium such as the SP-4 medium. Furthermore, this labelling procedure with uracil exhibits satisfactory specificity, since only the microorganisms can incorporate uracil.

Other markers may replace uracil provided that they possess the desired specificity with respect to microorganisms.

When attempts to detect the presence of mycoplasmas are made on a culture of lymphocytes inoculated previously with mycoplasmas as described above, it is also possible to detect the presence of mycoplasmas by the placing of the composition likely to contain these mycoplasmas in contact with a reagent containing at least one antibiotic with activity against mycoplasmas, in particular one of the quinolone family, followed by the detection of a possible reaction between the above composition and the antibiotic(s).

It is possible to use macrolides or cyclins, in addition to the antibiotics of the quinolone family.

According to another embodiment of the invention, the detection of the mycoplasmas corresponds to that of their nucleic acid. In this respect, the invention relates to a procedure of in vitro detection, characterized in that the composition likely to contain the mycoplasmas is treated so as to make the DNA of the mycoplasmas accessible to the reagent comprising a probe containing a DNA sequence itself derived from a highly conserved sequence in the ribosomal RNA characteristic of mycoplasmas.

In the case of the detection of the DNA, it is possible to start with the plasma or infected lymphocytes such as are obtained from a biological fluid taken from a patient.

Prior to the separation of the DNA, an amplification step may be desirable, for example in a SP-4 medium, until a concentration of mycoplasmas of $10^8$/ml is obtained.

In order to make the DNA accessible, the culture of mycoplasmas is advantageously subjected to centrifugation and the centrifugation pellet recovered is digested with a mixture of proteinase K and SDS. Thus, in order to detect the DNA of mycoplasmas, an advantageous procedure according to the invention is carried out as follows:

the culture containing the mycoplasmas is centrifuged under conditions leading to the sedimentation of the mycoplasmas and, if necessary, after an amplification step in a culture medium specific for mycoplasmas, the centrifugation pellet is treated in order to recover the DNA, for example with a mixture of proteinase K and SDS, the DNA thus obtained is placed in contact with the reagent comprising at least one probe containing a DNA sequence itself derived from a highly conserved sequence in the ribosomal RNAs characteristic of the mycoplasmas.

In order to implement the detection procedure for the DNA of the mycoplasmas, different probes may be used. As an example, mention is made of the probe pMC5 corresponding to the operon of the ribosomal RNA of *M. Capricolum* (D. Amikam et al., Ribosomal RNA genes in Mycoplasma, Nucleic Acids Research -1982- vol 10 No. 14 pp. 4215–4222). The hybridization reaction takes place after digestion of the DNA to be detected by the enzymes EcoRI and HindIII.

After having demonstrated the presence of mycoplasmas in the composition tested, it is also possible to choose to use probes exhibiting a high specificity towards one species of mycoplasma suspected to be responsible for the infection, in order to identify more precisely the nature of the mycoplasma and thus make provision for a more specific treatment. For example, in the case of an infection with mycoplasmas associated with an infection with the HIV virus, it will be advantageous to make use of probes such as those obtained from the strains of mycoplasmas *M. fermentans* No. 8 and the strain ber.

The object of the invention is also the application of these procedures for the detection of any infection due to mycoplasmas, in particular in the blood of a patient. Also included within the framework of the invention is a test for the in vitro study of the sensitivity to one or more given antibiotics of mycoplasmas isolated previously from a biological sample taken from a patient likely to be infected with a AIDS, characterized in that, the cell culture contaminated with the isolated mycoplasma(s) is incubated with increasing doses of various antibiotics, this culture is labelled, for example, with radioactive uracil, the radioactivity of each fraction is determined after sedimentation of the supernatant under conditions leading to the separation of the mycoplasmas from the other constituents.

Advantageously, the supernatant is sedimented to equilibrium in a sucrose density gradient and the radioactivity of each fraction is determined after precipitation, for example with 5% TCA.

If necessary, the surface area of the peaks corresponding to the density of mycoplasmas is calculated in comparison with a control untreated with antibiotics in order to determine the percentage of inhibition of the growth of the culture.

The performance of this test makes it possible to determine which of the known antibiotics possesses an activity against the mycoplasmas which is of value in the treatment of patients affected by these mycoplasmas. Particularly useful antibiotics for the treatment of infections due to mycoplasmas are, for example, antibiotics of the quinolone family, cyclins or macrolides.

The above sensitivity test may also be conducted in order to determine the appropriate doses required in the administration of the treatment. This test may also be of value in the follow-up of the efficacy of a given treatment with a selected antibiotic.

The sensitivity test previously described may also be used to study the possible efficacy of novel antibiotics towards the mycoplasmas detected and held responsible for a particular disease.

Other characteristics and advantages of the invention will become apparent in the figures and examples which follow.

The invention also relates to an immunogenic composition, characterized in that it contains at least one mycoplasma according to the invention. It also relates to antibodies, in particular monoclonal antibodies, characterized in that they recognize the mycoplasmas of the invention. These antibodies are prepared by standard procedures, for example, by fusion of spleen cells of an animal previously immunized with a given mycoplasma with a defined myeloma in order to form a hybridoma, the culture of the hybridoma and recovery of the antibodies formed.

Procedures are also described below in relation to the legends to the FIGS. 1 and 2.

1/ Isolation procedures 10 ml of blood are taken from a patient under heparin and centrifuged on a layer of Percoll (Seromed) at 400 g for 30 minutes.

a) the pellet of red blood cells is washed with RPMI 16–40 medium supplemented with 10% fetal calf serum (decomplemented beforehand by heating at 56° C. for 30 minutes and previously tested for the absence of mycoplasmas) and supplemented with antibiotics inactive towards the mycoplasmas (penicillin 100 U/ml, streptomycin 100 µg/ml). 50 ml of red blood cells resuspended in the RPMI 16–40 medium are incubated in the same medium for 18 hours at 37° C. at a concentration of $10^8$ red blood cells/ml. The red blood cells are then sedimented by centrifugation at 1000 g for 5 minutes, and the supernatent is ultracentrifuged at 245,000 g for 60 minutes.

The pellet possibly containing the mycoplasmas is resuspended in 1 ml of culture medium and inoculated into tubes containing SP-4 medium (Science 1977, 195, 892–894 Tully et al.), an enriched synthetic medium for the culture of mycoplasmas, on the one hand, and, on the other, into cultures of lymphocytes from normal donors seronegative for HIV and uncontaminated with mycoplasmas, stimulated by PHA and cultivated in complete RPMI 16–40 medium supplemented with 20 U/ml of interleukin 2.

One part of the red blood cells is also kept for a direct demonstration of the mycoplasmas according to procedures described below.

b) The band of the mononucleated white cells from the Percoll gradient is also washed by centrifugation and one part is placed in culture in complete RPMI 16–40 medium +Il2 after three days of activation with PHA as described above. Another part is directly inoculated into tubes containing SP-4 medium.

c) Finally, 3 ml of plasma are ultracentrifuged at 245,000 g for 60 minutes and the pellet stored for the extraction of DNA.

2/Detection of the mycoplasmas and tests of sensitivity towards antibiotics

In addition to the standard procedures (growth in synthetic media, such as the SP-4 medium), the following rapid and ultrasensitive procedure can be used:

Activated lymphocytes placed in culture (see above) are labelled for 3 hours with tritiated uracil (20 µCi/ml, Amersham). The supernatant is sedimented to equilibrium in a sucrose density gradient (70–20%, 1 hr at 45,000 rev/mn in a SW56 rotor (PBS buffer+2% fetal calf serum). Only microorganisms can incorporate uracil. The mycoplasmas form a band of a density varying from 1.18 to 1.24 (FIG. 1A and 1B). The labelling is inhibited by antibiotics active against the mycoplasmas, such as the quinolones or the tetracyclins.

The mycoplasmas can be passed to other stimulated lymphocytes or lymphoid lines such as the CEM line (Clone 13), possible contaminating mycoplasmas having been eliminated from this latter by prolonged treatment with antibiotics.

In order to determine rapidly the sensitivity of a mycoplasma thus isolated to antibiotics, the following procedure may be used:

Cell cultures contaminated with the mycoplasma are incubated for 48 hours with increasing doses of various antibiotics (cyclins, quinolones, macrolides). Then labelling with tritiated uracil is carried out for 3 hours as described above, followed by equilibrium sedimentation in a sucrose gradient. The radioactivity of each fraction is determined after precipitation by means of 5% TCA. The surface area of the peaks corresponding to the density of the mycoplasmas ($>1.18$) is calculated in comparison with the control untreated with antibiotics, and it is thus possible to determine percentages of inhibition. FIG. 2 is representative of such a determination carried out on a mycoplasma isolated from a patient.

3/Molecular cloning of the DNA of mycoplasmas and use of probes for the diagnosis Several types of mycoplasmas isolated from patients suffering from AIDS or asymptomatic carriers have been shown to be different with respect to their biological and molecular properties from the mycoplasmas described hitherto in man.

In particular, it has been possible to distinguish a novel species of mycoplasma, isolated in particular from two patients unrelated to each other by means of the analysis of restriction fragments of the ribosomal genes.

The mycoplasma ber was isolated from lymphocyte cultures taken from a patient suffering from AIDS. The mycoplasma culture was amplified to a concentration of $10^8$/ml in the synthetic medium SP-4. 200 ml were centrifuged and stored at $-80°$ C. after being washed with PBS buffer. After rapid thawing, the pellet is immediately digested with a mixture of proteinase K and SDS (150 mM, NaCl 10 mM Tris/HCl, pH 8.0, 10 mM EDTA, 0.5% mg/ml Proteinase K) in a ratio of 0.1 ml of the mixture per $10^8$ cells for a period of 1 hour at 55° C., followed by 6 hours at 37° C. About 300 µg of DNA were usually recovered from $10^{10}$ cells. This DNA is analysed by the procedures of "Dot-blot", restriction analysis, Southern transfer and hybridization, a detailed description of which will be found in the reference Amikam et al. (J. of Bact. 1984 vol. 158 p. 376–378).

The probe used, pMC5, corresponding to the operon of ribosomal RNA of *M. capricolum* (Amikam et al., Nucl. Ac. Res. 1982, vol. 10, No. 14 pp. 4215–4222) is capable of recognizing the corresponding ribosomal sequences of the mycoplasmas very efficiently after digestion by the enzymes EcoRI and HindIII.

The results of Southern analysis on agarose gel after digestion of the ribosomal operons of various isolated human mycoplasmas by these two enzymes are as follows: mycoplasma No. 8 shows a profile identical with that of the two strains *M. fermentans* and *M. incognitus* (this latter being only in fact a strain of *M. fermentans*) and is consequently called *M. fermentans* No. 8. On the other hand, the DNAs of the mycoplasmas ber and vuc show an identical profile and one which is identical with that given by the species *M. pirum*, indicating that the mycoplasmas ber and vuc are strains of the species *M. pirum*. The profiles of the mycoplasmas ber and vuc are different from those given by the following mycoplasmas: *M. orale, M. capricolum, M. pneumoniae, M. arginini, M. gallisepticum, A. laidlawii, A. axanthum, A. granularum, Ureaplasma urealyticum, Spiroplasma citri, M. genitalium, M. hominis, M. fermentans* (Table No. 1).

The DNA of *Mycoplasma fermentans* No. 8 and that of *M. ber* were cloned in a plasmid Blue script II (Stratagen), after digestion by EcoRI. 150 clones of 1000 to 2000 bp were obtained and those unable to hybridize with the most conserved regions of the mycoplasmas were selected. Specific molecular clones of *M. ber* and *M. fermentans* were thus obtained and sequenced. These sequences make it possible to deduce specific primer oligonucleotides for the PCR (polymerase chain reaction). Thus it is possible to apply the PCR and the Dot blots to the therapeutic follow-up of patients infected with this type of mycoplasma and receiving an antibiotic treatment designed to cure them of this infection.

The biological properties of *M. ber* and *M. fermentans* No. 8 are summarized in the following Table 2.

TABLE 1

| ORGANISM | ECORI No. of hybridization bands | ECORI Size of the hybridized chromosomal segment (kb) | HINDIII No. of hybridization bands | HINDIII Size of the hybridized chromosomal segment (kb) |
|---|---|---|---|---|
| *Mycoplasma-orale (ATCC 23714) | 1 | 5 | NA | NA |
| *Mycoplasma capricolum (ATCC 27343) | 2 | 4.8; 2 | NA | NA |
| *^Mycoplasma pneumoniae strainFH and M129-B16) | 1 | 9 | 3 | 1.65; 1.35; 0.75 |
| *Mycoplasma arginini (G-230) | 2 | 4; 7 | NA | NA |
| *Mycoplasma galllsepticum (strain S6) | 1 | 8 | NA | NA |
| *Mycoplasma gallisepticum (strain A5969) | 3 | 8; 8.2; 9 | NA | NA |
| *Acholeplasma laidlawli (oral strain) | 2 | 5.2; 8.8 | NA | NA |
| *Acholeplasma axanthum | 2 | 6.4; 7 | NA | NA |
| *Acholeplasma granularum | 2 | 6.9; 9.6 | NA | NA |
| *Ureaplasma urealyticum | 4 | 2.5; 6.2; 8.2; 12 | NA | NA |
| *Spiroplasma citri (Maroc R8A2) | 1 | 13 | NA | NA |
| *Mycoplasma genitalium | 2 | ca. 2.4; ca. 4.8 | NA | NA |
| ^Mycoplasma hominis | 3 | 1.5; 9.36; 13 | 2 | 3.5; 10.4 |
| ^Mycoplasma fermentans (PG-18) | 3 | 1.55; 4.4; 6.36 | 3 | 1.46; 2.63; 3 |
| ^Mycoplasma fermentans (K7) | 3 | 1.52; 4.4; 6.2 | 3 | 1.43; 2.6; 3 |
| ^Mycoplasma incognitus | 3 | 1.47; 3.67; 5.8 | 3 | 1.43; 2.42; 2.9 |
| ^Mycoplasma pirum | 3 | 2.3; 3.65; 5.45 | 3 | 1.25; 2.42; 1.8 |
| ^Ber | 3 | 2.3; 3.65; 5.45 | 3 | 1.25; 1.35; 1.8 |
| ^Vuc | 3 | 2.3; 3.65; 5.45 | 3 | 1.25; 1.35; 1.8 |
| ^No 8 | 3 | 1.49; 4 16; 6.49 | 3 | 1 44; 2.55; 3 |

TABLE 1: hydridization schema after digestion with Hind III or Eco RI of the DNA of different genomes of mycoplasmas isolated from patients with SIDA using pMC5 containing the rRNA of *M. capricolum* as probe
N.A.: not available

| BIOLOGICAL PROPERTIES OF THE MYCOPLASMAS No. 8 AND BER: | | | | | |
|---|---|---|---|---|---|
| Growth on SP-4 | Duration of the culture* | Fermentation of glucose | Hydrolysis of arginine | Sensitivity to digitonin | "Fried egg" colonies |
| yes | 7 days | yes | yes | yes | no |
| yes | 5 days | yes | yes | yes | no |

* Time taken by the culture to turn Phenol red to yellow with an inoculum of 1/10 of the ideal volume

BRIEF DESCRIPTION OF FIGURES

Legend to FIGS. 1A and 1B:

Detection of mycoplasmas, the existence of which is presumed on the basis of the density gradient procedure using uracil as marker.

10–15 ml of heparinized blood are centrifuged at 400 g in a Percoll gradient for 30 minutes. The pellet of red blood cells is washed with culture medium (RPMI 16–40+10% of decomplemented fetal calf serum+penicillin 100 U/ml, streptomycin 50 µg/ml).

The washed erythrocytes are incubated for 18 hours at 37° C. in the same medium (to which had been added or are added 20 U of Il 2) at a concentration of $10^8$ T lymphocytes of a healthy donor per ml, and stimulated by $5\times10^5$/ml of PHA.

The coculture is then incubated for 3 hours in the presence of 20 Ci/ml of $^3$H uracil (AMERSHAM 44 Ci/ml).

After addition of 3 mM of sodium azide, the cells are sedimented at 1000 g for 5'. One part of the clarified supernatant (1 ml) is sedimented in a 20–70% sucrose gradient in a PBS buffer supplemented with 2% fetal calf serum at 245,000 g for 60 minutes in a BECKMANN SW56 rotor.

Aliquots of the collected fractions were sampled for density measurements using a refractometer. The remainder is precipitated with 5% TCA and subjected to counting in a scintillation spectrometer (LKB).

All of the centrifugations were performed preferably at 40° C. under sterile conditions. The sucrose solutions were autoclaved.

Controls were carried out consisting of a sucrose sradient only, and the T lymphocyte supernatant only. No peaks were observed.

Figure 2A:
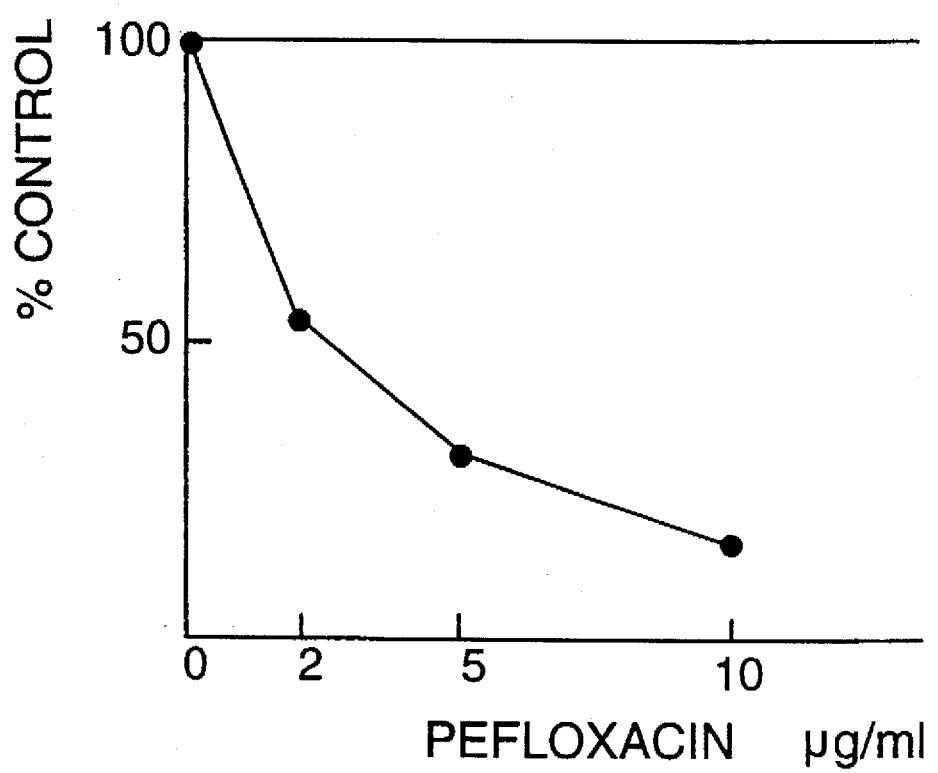
Figures 2B, 2C:
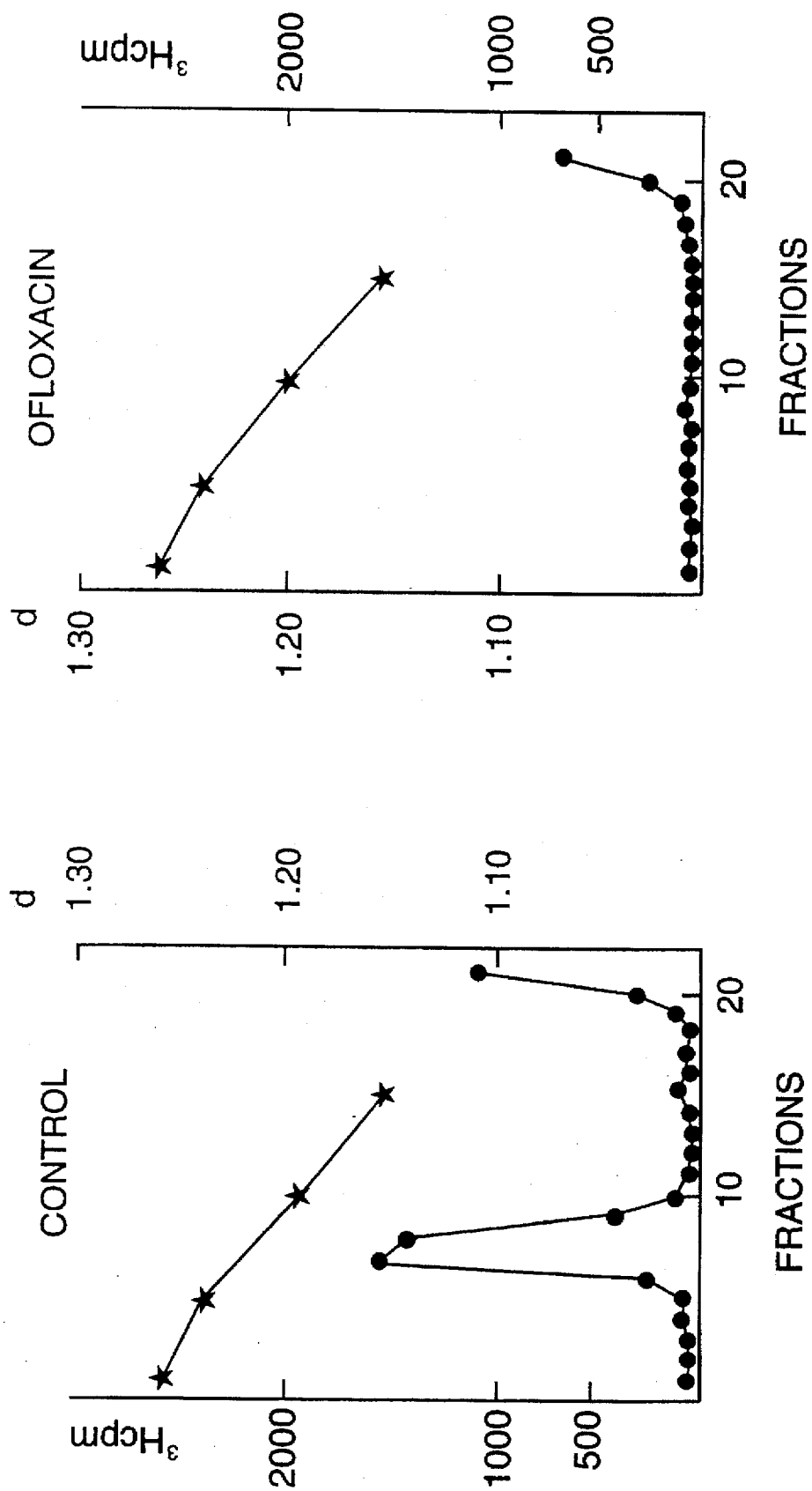

Legend to FIGS. 2A, 2B, and 2C:

Sensitivity of M. pirum isolated from the serum of a patient (BER) to antibiotics.

CEM/13 cells, subjected to prior cultivation for three weeks in the presence of 0.5 µg/ml of MRA ("Mycoplasma Removal Agent") were tested for absence of contamination by mycoplasmas. They were used to prepare cultures of M. pirum.

Figures 1A, 1B:
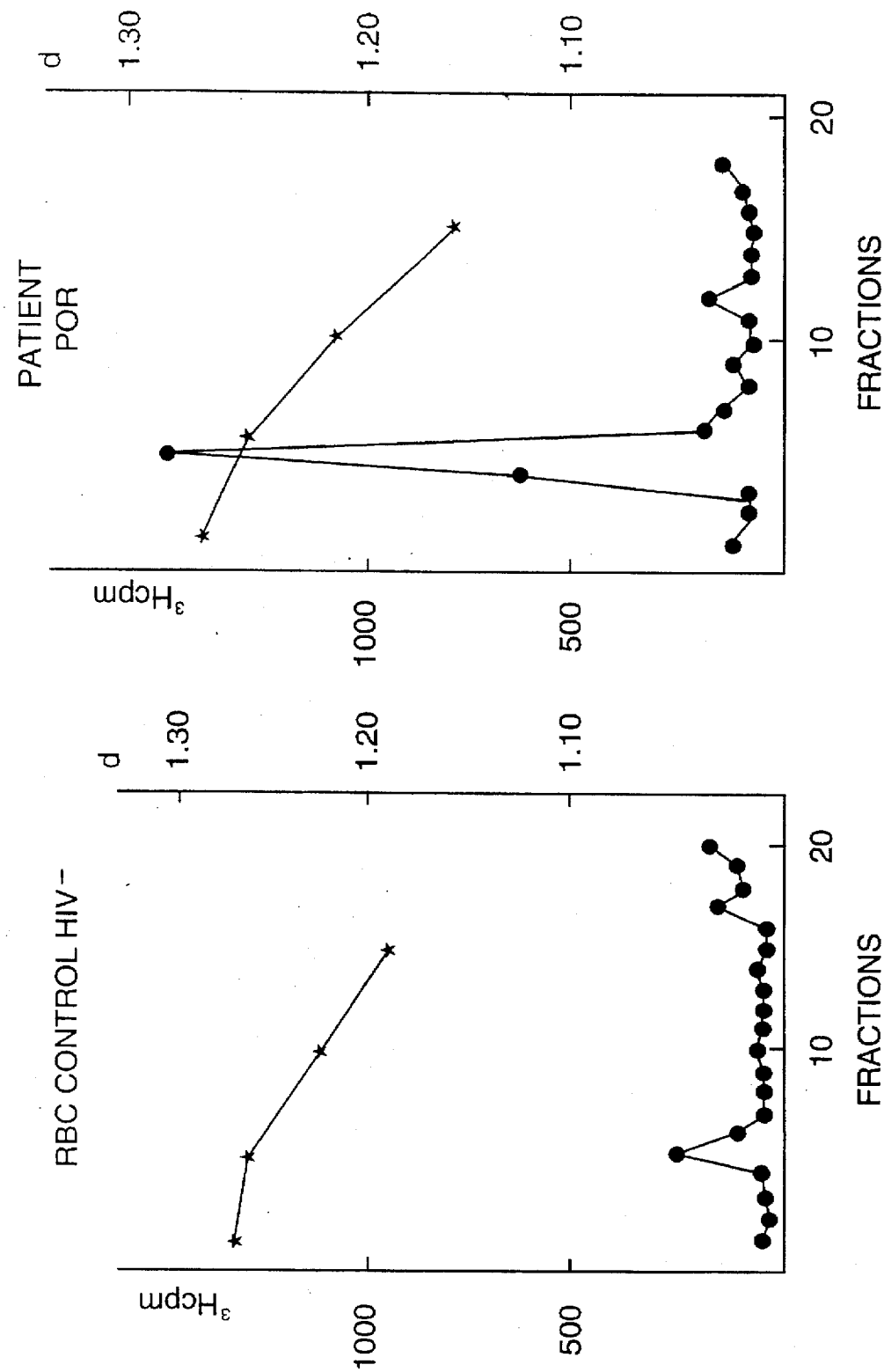

After one week of culture, the cells were incubated in the presence of antibiotic for 48 hours, then labelled for 3 hours with $^3$H uracil as described in FIG. 1A and 1B.

The cell supernatant is analysed in a sucrose gradient, also as indicated in FIG. 1A and 1B.

The surface area of the peak of mycoplasmas (fractions of densities included in the range 1.18 to 1.24) is measured and expressed in % of untreated controls.

Above: dose response curve for pefloxacin.

Below: two examples of analysis in a sucrose gradient:
untreated controls (on the left) and cells treated with 5 µg/ml of ofloxacin.

The curve on the left corresponds to a healthy donor: see small peak at p=1.24.

The curve on the right corresponds to cells in the serum of a patient with AIDS, infected with the virus as a result of a sexual contact.

Ref. for pMC5: D. Amikam, S. Razin and G. Glaser. Ribosomal RNA genes in Mycoplasma—Nucleic Acid Research (1982) vol. 10 No. 14 pp. 4215–4222.

Antibiogram/mycoplasmas:

In: Methods in Mycoplasmology, vol. II. "Antibiotic sensitivity testing of mycoplasmas" by L. B. Senterfit. J. G. Tully, S. Razin eds. Academic Press, Inc. New York.

We claim:

1. An in vitro method of detecting the presence of M. pirum strain ber infection in a person suspected of having said infection, wherein said person is also infected with the human immunodeficiency virus (HIV), said method comprising,
   contacting nucleic acid from a biological sample from said person with a nucleic acid probe pMC5 that binds specifically to nucleic acid of M. pirum strain ber; and
   detecting hybridization of said probe to the nucleic acid of said biological sample.

2. The method of claim 1 wherein said nucleic acid probe is pMC5, which has the nucleotide sequence of the operon of ribosomal RNA of M. capricolum, and wherein the nucleic acids of said mycoplasma are digested with EcoRI and HindIII.

3. The method of claim 1, wherein said biological sample is plasma.

4. The method of claim 3, wherein said biological sample is lymphocytes infected with the human immunodeficiency virus (HIV).

5. The method of claim 4, wherein said lymphocytes are grown in culture, the mycoplasma is isolated from said culture by centrifugation to form a pellet, said pellet is treated to release said nucleic acid, and said nucleic acid is placed in contact with said nucleic acid probe.

6. An in vitro method of detecting the presence of M. fermentans infection in a person suspected of having said infection, wherein said person is also infected with the human immunodeficiency virus (HIV), said method comprising,
   contacting nucleic acid from a biological sample from said person with a nucleic acid probe that binds specifically to nucleic acid of M. fermentans No. 8; and
   detecting hybridization of said probe to the nucleic acid of said biological sample.

7. The method of claim 6, wherein said biological sample is plasma.

8. The method of claim 7, wherein said biological sample is lymphocytes infected with the human immunodeficiency virus (HIV).

9. The method of claim 8, wherein said lymphocytes are grown in culture, the mycoplasma is isolated from said culture by centrifugation to form a pellet, said pellet is treated to release said nucleic acid, and said nucleic acid is placed in contact with said nucleic acid probe.

* * * * *